US007654964B1

(12) United States Patent
Kroll et al.

(10) Patent No.: US 7,654,964 B1
(45) Date of Patent: Feb. 2, 2010

(54) SYSTEM AND METHOD FOR DETECTING ARTERIAL BLOOD PRESSURE BASED ON AORTIC ELECTRICAL RESISTANCE USING AN IMPLANTABLE MEDICAL DEVICE

(75) Inventors: Mark W. Kroll, Orono, MN (US); Ashok Kaul, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 501 days.

(21) Appl. No.: 11/378,604

(22) Filed: Mar. 16, 2006

(51) Int. Cl.
*A61B 5/02* (2006.01)
(52) U.S. Cl. .................. 600/486; 600/481; 600/485
(58) Field of Classification Search ............. 600/486, 600/547
See application file for complete search history.

(56) References Cited

U.S. PATENT DOCUMENTS

| 5,267,566 | A | * | 12/1993 | Choucair et al. ............ 600/488 |
| 5,476,484 | A | * | 12/1995 | Hedberg ...................... 607/23 |
| 5,707,400 | A | * | 1/1998 | Terry et al. .................. 607/44 |
| 6,314,323 | B1 | | 11/2001 | Ekwall ......................... 607/23 |
| 6,718,190 | B2 | * | 4/2004 | Krivitski et al. ............. 600/322 |
| 2003/0158584 | A1 | | 8/2003 | Cates et al. ..................... 607/2 |
| 2005/0267379 | A1 | * | 12/2005 | Pfeiffer et al. .............. 600/526 |

* cited by examiner

*Primary Examiner*—Patricia C Mallari

(57) ABSTRACT

Techniques are provided for use with a pacemaker or other implantable medical device for detecting arterial blood pressure. Briefly, the pacemaker detects aortic electrical resistance using sensing/pacing leads. Aortic electrical resistance pertains to the resistance to an electrical current passing through the aorta. The pacemaker then determines the arterial blood pressure of the patient based on the aortic resistance and a predetermined calibration value that relates aortic resistance to arterial pressure. The calibration value is updated monthly based on blood pressure values detected using an external blood pressure sensor employing a blood pressure cuff. Other techniques described herein pertain to the determination of other physiologic parameters such as stroke volume and cardiac output and to the detection of changes in hematocrit. Any of the various physiological parameters may then be used to trigger or control warning signals and responsive therapy.

16 Claims, 14 Drawing Sheets

SYSTEM AND METHOD FOR DETECTING ARTERIAL BLOOD PRESSURE BASED ON AORTIC ELECTRICAL RESISTANCE USING AN IMPLANTABLE MEDICAL DEVICE

FIELD OF THE INVENTION

The invention generally relates to implantable medical devices, such as pacemakers or implantable cardioverter-defibrillators (ICDs), and in particular to techniques for measuring blood pressure within a patient in which a medical device is implanted.

BACKGROUND OF THE INVENTION

A pacemaker is implantable cardiac stimulation device for implant within a patient that analyzes an intracardiac electrogram (IEGM) to detect various arrhythmias such as an abnormally slow heart rate (bradycardia) or an abnormally fast heart rate (tachycardia) and delivers electrical pacing pulses to the heart in an effort to remedy the arrhythmias. An implantable cardioverter-defibrillator (ICD) additionally detects atrial fibrillation (AF) or ventricular fibrillation (VF) and delivers electrical shocks to terminate fibrillation.

State of the art pacemakers and ICDs are also capable of detecting and tracking a wide range of physiological parameters relevant to the health of the patient. One parameter of particular interest is arterial blood pressure, which is relevant to a variety of medical conditions such as hypotension. However, it is difficult to reliably measure arterial blood pressure with a pacemaker or ICD. Heretofore, some attempts have been made to develop implantable blood pressure sensors employing piezoelectric devices, or the like, but with limited success. Such sensors can clog or otherwise degrade over time. One example of a technique for sensing blood pressure via an implantable medical device is described in U.S. Patent Application 2003/0158584 of Cates et al., entitled "Chronically-Implanted Device for Sensing and Therapy." In view of the problems arising with implantable blood pressure sensors, arterial blood pressure is usually detecting using an external blood pressure sensor, such as conventional blood pressure cuff-based device. Although external sensors can provide accurate measurement of arterial blood pressure, such measurements are, at best, infrequent. In addition, with blood pressure detector externally, the pacemaker or ICD cannot utilize the detected blood pressure value to automatically adjust therapy, unless the value is also automatically transmitted to the device. Conventional external blood pressure sensors do not provide that capability.

It would be far preferable to provide a technique for continuously detecting arterial blood pressure using a pacemaker or ICD. Ideally, such a technique would utilize an external blood pressure sensor only for occasional recalibration. Moreover, such a technique would preferably not require any sensors to be implanted within patient arteries. In particular, it would be highly desirable to provide a technique for detecting arterial blood pressure using a pacemaker or ICD that can exploit otherwise conventional pacing leads. The present invention is directed to providing just such a technique.

Once arterial blood pressure has been detected, it can be used in combination with other parameters, such as heart rate, to detect stroke volume and cardiac output within the patient. Cardiac output is a particularly important parameter to track within patients with congestive heart failure (CHF) or within patients who are at risk of CHF. Hence, additional aspects of the invention are directed to detecting stroke volume, cardiac output and other physiological parameters in conjunction with the detection of arterial blood pressure.

SUMMARY

Techniques are provided for use with an implantable medical device for detecting blood pressure. Briefly, a value representative of aortic electrical resistance (R) is detected within the patient. Aortic electrical resistance pertains to the resistance to an electrical current passing through the aorta. Then, the arterial blood pressure is determined within the patient based on the aortic resistance value (R). Preferably, the aortic resistance value is detected using otherwise conventional pacing/sensing leads. In this manner, the implanted device is capable of detecting the arterial blood pressure of the patient based on signals sensed using otherwise conventional pacing/sensing leads. Hence, specialized sensors need not be implanted within the arteries of the patient. In a preferred implementation, arterial pressure (P) is determined from aortic resistance (R) using at least one calibration value (K), which relates aortic resistance to arterial blood pressure within the patient. Preferably, the calibration value is updated monthly based on arterial blood pressure values detected using an external blood pressure sensor employing a blood pressure cuff. Hence, the external blood pressure detector is utilized only relatively infrequently, e.g. only once a month.

In one particular implementation, the implantable medical device is a pacemaker or ICD that includes a right atrial (RA) tip electrode and a device housing electrode positioned generally on opposing sides of the aorta of the patient. Aortic electrical resistance (R) is detected by measuring the electrical resistance between the RA electrode and the device housing electrode along a vector extending through the aorta. The detected resistance value is affected by the width of the aorta, which is in turn affected by the pressure of blood within the aorta. In other words, aortic electrical resistance is correlated with, and affected by, the arterial blood pressure within the patient. The aforementioned calibration value (K) relates particular aortic resistance values to particular arterial pressure values to permit the current arterial pressure within the patient to be derived from a current value of aortic resistance. In use, the latest value of K is retrieved from device memory. Patient arterial blood pressure (P) is then determined based on the detected aortic resistance (R) and the calibration value (K) by calculating: $P=K/R$. Aortic resistance (R) is preferably detected substantially continuously to permit the arterial blood pressure to also be determined substantially continuously.

Preferably, the calibration value (K) is calculated once per month using an arterial blood pressure value detected using the external blood pressure detector. More specifically, once per month, the external detector detects the current arterial blood pressure of the patient (P') and transmits that value to the implanted device. The implanted device simultaneously detects the current aortic resistance (R') of the patient using the pacing/sensing leads and then calculates the calibration value (K) using $K=P'R'$. In this manner, the calibration value (K) is updated once per month based on an externally detected blood pressure value to recalibrate the implanted system so as to maintain accurate arterial blood pressure detection based on aortic resistance (R) values.

The implanted device may also be equipped to determine the stroke volume of the patient based, in part, on the detected arterial blood pressure (P). In one particular example, once per month, an external system is used to determine the systemic resistance ($R_a$) of the patient. The latest value for $R_a$ is transmitted to the implanted device and stored therein. Arterial blood pressure (P) is then repeatedly calculated by the implanted device using the aforementioned techniques over the course of a single cardiac cycle (i.e. heartbeat). The stroke volume of the patient is then calculated from $R_a$ and the arterial pressure values based on a discrete computational version of:

$$\text{stroke volume} = \int_{start}^{end} \frac{P(t)}{R_a} dt$$

where P(t) represents arterial blood pressure as a function of time through a single cardiac cycle, $R_a$ represents the systemic resistance, "start" represents the time at the start of the cardiac cycle and "end" represents the time at the end of the cardiac cycle. Alternatively, the systemic resistance is also measured as a function of time throughout the cardiac cycle, i.e. $R_a(t)$ is measured. In any case, stroke volume can thereby be determined within the patient. The cardiac output of the patient can then be detected based on stroke volume and heart rate. In one example, patient heart rate is determined based on IEGM signals sensed using the pacing/sensing leads. Cardiac output is then calculated by multiplying the current stroke volume by the current patient heart rate. Changes in patient cardiac output are tracked and appropriate warning signals are generated if the cardiac output decreases by an amount indicative of CHF.

Changes in patient hematocrit (i.e. the proportion, by volume, of the blood that consists of red blood cells) can also be evaluated based on detected values of aortic resistance. In one example, aortic resistance is determined at two different frequencies using the pacing/sensing leads and the difference between the two aortic resistance values is calculated. Changes in hematocrit are then evaluated by detecting any changes in the difference between the two aortic resistance values over time.

Thus, various systems and methods are provided for detecting arterial blood pressure, stroke volume, cardiac output, and hematocrit and related physiological parameters using an implantable medical device.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
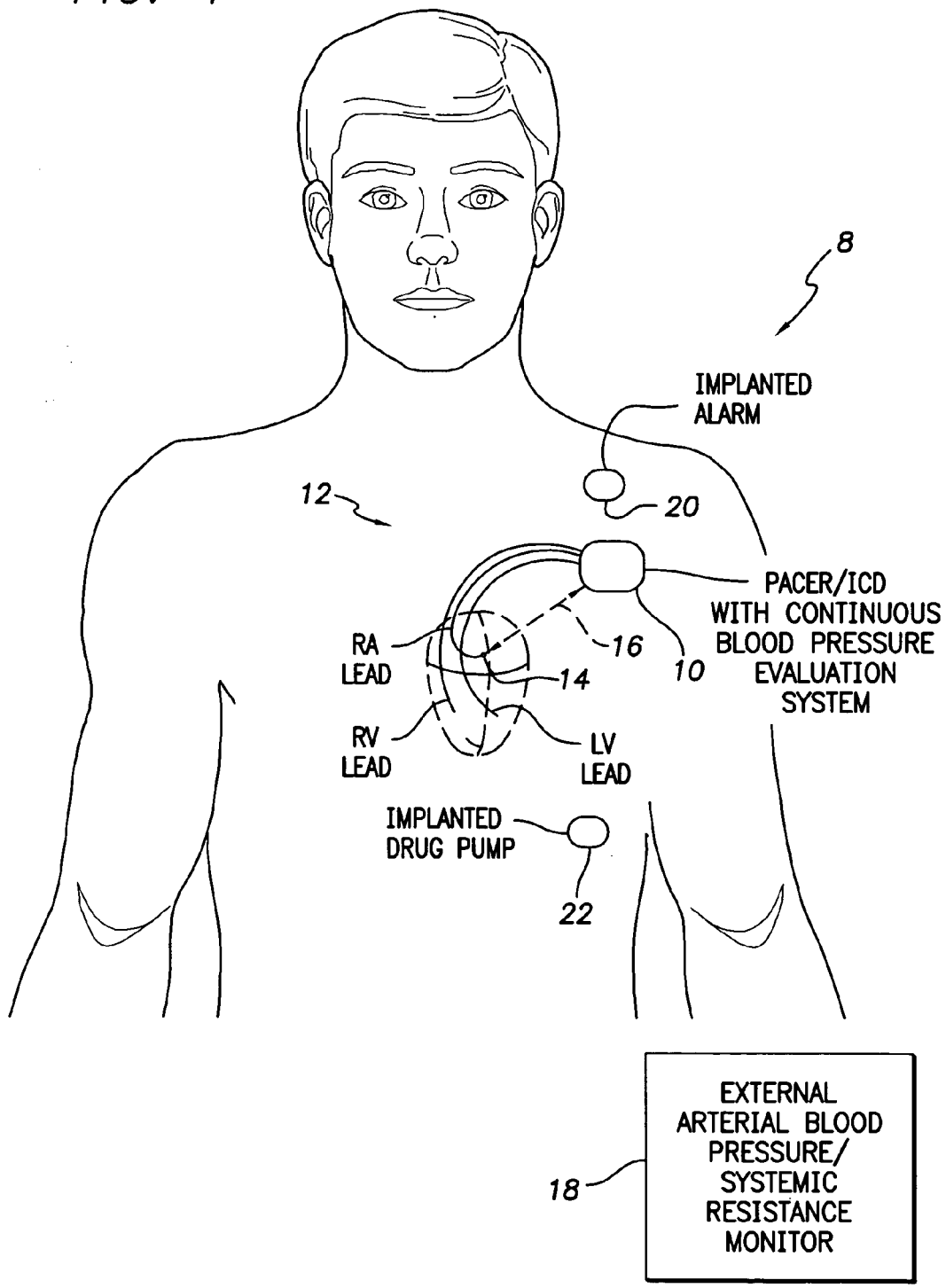
FIG. 1 illustrates pertinent components of an implantable medical system having a pacemaker or ICD capable of detecting arterial blood pressure and other parameters based on aortic electrical resistance.

FIG. 1 illustrates an implantable medical system 8 capable of detecting arterial blood pressure and related physiological parameters such as cardiac output and hematocrit using aortic resistance-based techniques. In the preferred implementation, the system is further capable of automatically controlling or delivering appropriate warning signals and therapy. Briefly, implantable medical system 8 includes a pacer/ICD 10 or other cardiac stimulation device that incorporates internal components (shown individually in FIG. 13) for detecting arterial blood pressure substantially continuously based on aortic resistance values sensed using pacing/sensing leads 12. More specifically, aortic electrical resistance is sensed based on electrical resistance values measured between an RA tip electrode 14 and a housing electrode of the pacer/ICD 10 that are positioned on opposing sides of the aorta. Hence, resistance values are measured along a sensing vector 16 that passes through the aorta (which is not separately shown in FIG. 1). Right ventricular (RV) and left ventricular (LV) leads are also shown in FIG. 1. A more detailed and complete illustration of the heart and lead system 12 is provided in FIGS. 12 and 13, and described below.

As will be explained in greater detail below, by sensing resistance along a vector passing through the aorta, values representative of aortic electrical resistance (R) can thereby be derived. The aortic resistance values are then used in combination with a predetermined calibration value (K) to calculate the arterial blood pressure (P) of the patient. The aortic resistance values may be updated substantially continuously based on newly detected resistance values so as to permit substantially continuous sensing of arterial blood pressure. By "substantially continuous," it is meant that blood pressure values are detected or updated at least once per cardiac cycle. This is in contrast with external blood pressure sensors that are typically used only once per hour or perhaps once per day or, in many cases, far less frequently than that. In some implementations of the invention, multiple resistance measurements are made within individual cardiac cycles to thereby permit even more frequent evaluation of systemic resistance. For example, dozens of resistance measurements may be made during a single cardiac cycle to permit changes in arterial blood pressure to be tracked over the course of a single heartbeat. In other implementations, the techniques of the invention are performed less frequently, such as only once every ten cardiac cycles or perhaps only once per minute. Hence, although the invention permits arterial blood pressure to be detected substantially continuously, there is no requirement that the pressure be detected that frequently. Rather, the techniques of the invention are equally applicable to infrequent, periodic detection and/or demand-based detection.

The aortic resistance-based arterial blood pressure detection technique performed by pacer/ICD 10 is preferably calibrated at least once per month based on arterial blood pressure values sensed using an external blood pressure monitor 18, which may be part of a bedside monitor equipped with an automatically inflatable blood pressure cuff (not shown.) The arterial blood pressure value sensed by the external monitor is transmitted via telemetry to the pacer/ICD 10, which calculates and stores the aforementioned calibration value (K). By updating the calibration value at least once per month, the arterial blood pressure detection procedure performed by the pacer/ICD is thereby recalibrated at least once per month so as to remain accurate. As will be explained below, changes in aortic compliance within the patient can affect the aortic resistance-based determination of arterial blood pressure. However, changes in aortic compliance typically occur, if at all, only quite slowly. Hence, recalibration once per month is typically sufficient to ensure accurate detection of the arterial blood pressure using the pacer/ICD. In other implementations, recalibration using the external system may be performed more or less frequently. Monthly recalibration is merely exemplary. In addition, as will be explained, the calibration value can be adjusted during the month based on changes in the autonomic tone of the patient to enhance detection accuracy.

In addition to detecting arterial blood pressure, the pacer/ICD may also be equipped to detect stroke volume and cardiac output. As will be explained further below, stroke volume is detected based on numerous arterial blood pressure measurements made during a single cardiac cycle, in combination with a systemic resistance value ($R_a$) received from the external monitor 18. Once stroke volume is determined, cardiac output is calculated by multiplying the stroke volume by the current heart rate. As will also be explained, changes in the hematocrit of the patient may be detected and tracked as well by the pacer/ICD. Any of the various parameters detected or tracked by the pacer/ICD may be used to control or adjust therapy or to trigger warning signals. For example, warning signals may be generated in response to a significant sustained change in arterial blood pressure. Warnings may also be generated in response to a significant sustained reduction in cardiac output, which may be indicative of CHF. The warnings signals may be delivered via an implanted warning device 20, which may be a voltage "tickle" warning device. Warnings may additionally and/or alternatively be relayed to the external system 18. Drug therapy may automatically be delivered using an implanted drug pump 22. Implantable drug pumps are discussed in U.S. Pat. No. 5,328,460 to Lord, et al., entitled "Implantable Medication Infusion Pump Including Self-Contained Acoustic Fault Detection Apparatus." Discussions of possible medications for use with selected conditions are provided below. Drug dosages provided by the drug pump may be titrated based on the severity of the detected condition. If warranted, pacing therapy may also be delivered by pacer/ICD 10 using leads 14. In particular, in response to a significant reduction in cardiac output, the pacer/ICD may be equipped to immediately initiate cardiac resynchronization therapy (CRT). Additionally, the pacer/ICD is preferably capable of performing a wide variety of otherwise conventional pacing and/or defibrillation functions, such as delivering pacing is response to an arrhythmia or generating and delivering defibrillation shocks in response to fibrillation.

Hence, FIG. 1 provides an overview of an implantable system capable of detecting arterial blood pressure and related physiological parameters based on aortic resistance and for delivering appropriate warnings and therapy. Embodiments may be implemented that do not necessarily perform all of these functions. Rather, embodiments may be implemented that provide, for example, only for the detection of arterial blood pressure but not detection of stroke volume or cardiac output. Systems provided in accordance with the invention need not include all the components shown in FIG. 1. In many cases, for example, no drug pump and no warning devices are implanted. No attempt is made herein to describe all possible combinations of components that may be provided in accordance with the general principles of the invention. In addition, internal connection lines for interconnecting the various implanted components are not shown. Alternatively, the various implanted components may communicate with one another via wireless communication techniques. Also, the particular shape, size and location of the implanted components shown in FIG. 1 are merely illustrative and may not necessarily correspond to actual implant locations. Preferred implant locations for the leads are more precisely illustrated in FIGS. 12 and 13.

Overview of Aortic Resistance-based Blood Pressure Detection Technique

Figure 2:
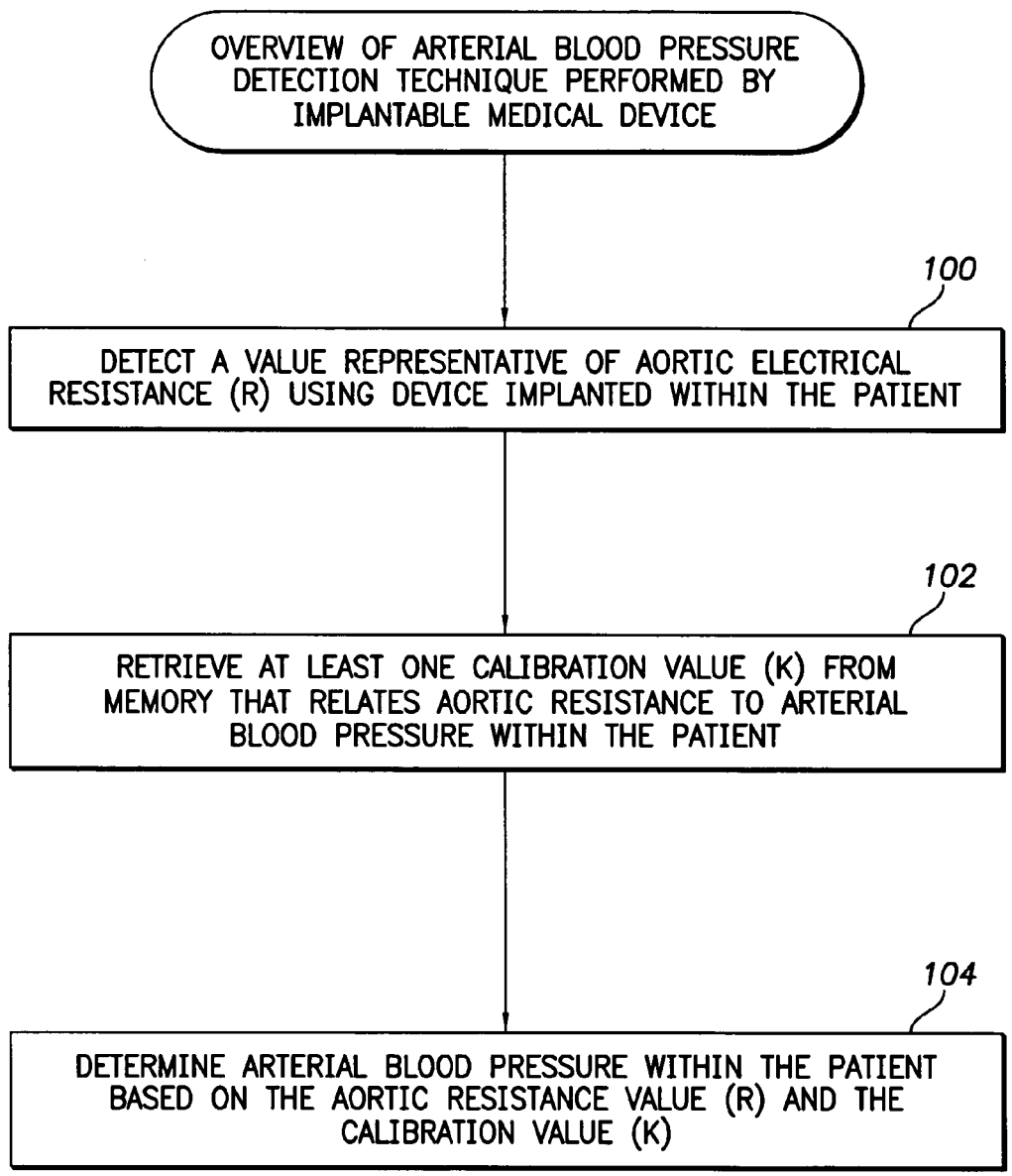
FIG. 2 provides an overview of an arterial blood pressure detection technique that may be performed by the implantable system of FIG. 1.

FIG. 2 provides an overview of an aortic resistance-based technique for detecting arterial blood pressure using pacer/ICD 10 of FIG. 1, or other implantable medical device. Initially, at step 100, the pacer/ICD detects a value representative of aortic electrical resistance (R), i.e. a value representative of the electrical resistance to an electrical current passing through the aorta. Preferably, aortic resistance is detected at a frequency above 5 kHz so that variations in hematocrit do not affect the resistance measurement. (Hematocrit is discussed more fully below in connection with FIG. 9.) The aortic resistance value is affected by the width of the aorta, which, in turn, is affected by the pressure of blood in the aorta. Hence, aortic resistance is related to, and affected by, arterial pressure. At step 201, the pacer/ICD retrieves at least one predetermined calibration value (K) from device memory that relates aortic resistance to arterial blood pressure within the particular patient. An exemplary technique for calculating a calibration value is set forth in FIG. 3 and will be described below. At step 104, the pacer/ICD then determines the arterial blood pressure (P) of the patient based on the aortic resistance value (R) detected at step 100 and the calibration value (K) retrieved at step 102. An exemplary technique for determining P from R and K is set forth in FIG. 4 and will be described below. Note that, in some cardiological literature, the term "resistance" is used to refer to systemic hydraulic resistance of the arterial tree. For example, the term "aortic resistance" is often used to refer to the aortic pressure divided by aortic flow, i.e. it is a measure of left ventricular afterload. Herein, resistance, per se, instead refers to electrical resistance. Resistance refers to electrical resistance.

Thus, the technique of FIG. 2 exploits the relationship between aortic resistance (R) and arterial pressure (P) to derive arterial pressure from aortic resistance. This relationship will now be more fully explained. Consider a cylindrical portion of an idealized aorta having a length (l) and a diameter D, i.e. a "right circular" cylinder. The sides of the portion of the aorta are formed of an elastic material having compliance (C), which is given in terms of ml/mmHg. The portion of the aorta is filled with blood having uniform blood resistivity ($\rho$) and a uniform pressure (P). Blood resistivity ($\rho$) may be expressed in units of ohm-centimeter ($\Omega \cdot cm$). The blood is regarded as being incompressible. Now consider an electrical current passing lengthwise through the portion of the aorta along its length (l). The electrical resistance (R) seen by the electrical current due to the blood in the aorta is then given by:

$$R = \frac{4l}{\pi D^2} \rho \quad (1)$$

Rearranging terms yields:

$$D^2 = \frac{4l}{\pi R} \rho. \quad (2)$$

Meanwhile, the volume (V) of the idealized portion of the aorta is given by V=PC. From simple geometry, volume (V) is also equal to $\pi l D^2/4$. Hence, the pressure (P) within the portion of the aorta is given $$P = \frac{\pi l D^2}{4C} = \frac{\pi l}{4C}\left[\frac{4l\rho}{\pi R}\right] = \frac{l^2 \rho}{RC} \quad (3)$$

Combining Equation (2) with Equation (3) permits the pressure (P) to be related to the resistance (R) as:

$$P = K/R \quad (4)$$

where $K = l^2 \rho / C$

Hence, the pressure within the cylindrical portion of the idealized aorta is inversely proportional to the electrical resistance. Within a non-idealized aorta, compliance C is not necessarily linear, nor is C uniform along the length of the aorta. Also, blood is not necessarily incompressible and is also not uniform. Hence, Equation (4) is only an approximation, albeit an accurate one. Assuming that blood resistivity ($\rho$), compliance (C) and length (l) do not change, then the calibration value (K) remains constant (i.e. K is independent of P and R.) As such, an increase is pressure results in a decrease in electrical resistance. Conversely, a decrease in pressure results in an increase in aortic resistance. In this regard, an increase in pressure of the incompressible blood in the idealized aorta results in an expansion of the aorta (which is at least somewhat compliant) thus increasing the diameter (D). From Equation (1), it is seen that an increase in the diameter (D) results in a decrease in electrical resistance (R). This is simply due to the presence of additional blood (which acts as a conductor) along the current path. The additional blood provides for a more conductive (i.e. a less resistive) current path. On the other hand, a decrease in pressure results in a decrease in diameter (D), thus decreasing the amount of blood along the current path and increasing electrical resistance. Note, though, in the above analysis, the actual value of diameter (D) is irrelevant to the relationship of pressure (P) to resistance (R), as the diameter (D) does not appear in Equation (4). Indeed, the actual shape of the aorta is largely irrelevant. That is, the above analysis—although based on a cylindrical portion of an idealized aorta—is equally applicable to an aorta with a more complex or irregular shape. Hence, Equation (4) provides a valid approximation of P regardless of the diameter and shape of the aorta. This is particularly true when the electrical resistance is measured along the length of the aorta, i.e. when the electrical current used to measure the resistance flows along the axis of the cylindrical portion of the aorta.

If the resistance is instead measured along a vector that passes through the aorta at an angle, then the analysis is somewhat more complicated. In particular, the length along which resistance is measured (i.e. l) is no longer independent of the diameter (D) of the aorta. Rather, an increase in the diameter (D) results in an increase in length (l) due to simple geometry. Hence, an increase in pressure (which causes an increase in D) likewise causes an increase in l, thus affecting the value of K. In other words, if the electrical current is at an angle to the axis of the aorta, then K is not truly independent of P, even in the idealized case. However, as already noted, Equation (4) merely provides an approximation of P anyway, since C and $\rho$ are not truly uniform. Equation (4) is approximately valid regardless of the angle through which the electrical current used to measure the resistance passes through the aorta. If desired, a more precise correlation formula may be used to correlate P to R, such as a formula of the form $P = K_2 + K_3/R$ where $K_2 + K_3$ are appropriately chosen coefficients. Quadratic or higher order correlation formulas may alternately be employed, but are typically not warranted.

Now considering the aorta within an exemplary human patient, aortic resistance (R) is measured by the pacer/ICD along a resistance vector that passes through the aorta between, e.g., the RA tip electrode and the device housing electrode. (See FIGS. 12 and 13, described below.) The portion of the vector passing through the aorta generally corresponds to length (l) in the above analysis. This vector is at an angle to the aorta and, depending upon the relative locations of the RA tip and the device case, the vector may pass through the aorta twice (once through the ascending aorta and once through the descending aorta) or may pass through the aortic arch. (The aortic arch is generally regarded as the curved portion of the aorta connecting the ascending aorta with the descending thoracic aorta. From the ascending aorta, the arch courses slightly leftward in front of the trachea and then proceeds posteriorly to the left of the trachea and the esophagus.) Equation (4) is still approximately valid, regardless of the angle through which the vector passes through the aorta and regardless of the location along the aorta through which the vector passes. Moreover, once the pacer/ICD and leads are implanted, neither the angle nor location along the aorta of the sensing vector significantly changes. Hence, length (l)

remains substantially constant, other than slight changes due to distension of the aorta itself, which do not adversely affect the approximation of P. Another embodiment, discussed later, has resistance sensing electrodes on the lead and closer to the heart giving a more direct line through the ascending aorta.

Furthermore, within human patients, blood resistivity (ρ) and aortic compliance (C) typically vary only rather slowly, if at all. Hence, over the short term (e.g. over a period of less than one month), K remains substantially constant. Thus, once K has been determined, it can be reliably used to relate aortic resistance to arterial pressure over the short term. Periodic recalibration of K, such as once per month, ensures that any slight changes in l, ρ and C occurring over time are automatically taken into account. Note that there is no need to ever actually calculate l, ρ or C. Rather, it is sufficient to obtain a value for K, which can be calculated based on known values of R and P. As will be explained more fully below with reference to FIG. 3, K may be calculated based on an arterial pressure value P' obtained from an external blood pressure sensor in combination with the aortic resistance R' sensed by the implanted device at the same time.

Note also that the vector between the RA tip electrode and the device housing passes through other tissue besides the aorta. Indeed, the aorta represents only a relatively small portion of the total tissue along the vector between the RA tip and the device housing. However, the characteristics other tissues, principally myocardial tissues and lung tissues, do not vary much over the short term. Hence, to the extent to which variations in the characteristics of these tissues affect the value of K, the affect is not significant in the short term. Any longer term variations are accounted for via the monthly recalibration of K. Furthermore, the resistivity of blood is much lower than that of the other tissues, i.e. blood is much more conductive that the other tissues. Human blood typically has a resistivity of only about 150 Ω·cm. Other body tissues typically exhibit significantly higher resistivity. Muscle has a resistivity of about 400 Ω·cm on average (with a lower value with the grain and higher against the muscle grain.) Fatty tissue has a resistivity of about 400 to 2000 Ω·cm. The highest resistivity within the body typically occurs in dry lung tissue filled with air, which is at about 2000 Ω·cm. The significant difference in resistivity between blood and other tissues ensures that relatively small variations in aortic diameter caused by variations in blood pressure are reflected in relatively large variations in the measured aortic resistance. More specifically, an increase in the diameter of the aorta will increase the length of the portion of the current vector that passes through blood, while also decreasing the length of the portion that passes through other tissues, since the total distance between the electrodes remains substantially the same. Hence, an increase in arterial pressure causes electrical resistance (measured along the current vector from RA tip to device case) to decrease both because (1) the portion of the current vector extending through the low resistivity blood of the aorta increases and (2) the portion of the current vector extending through the other high resistivity tissues decreases. This tends to enhance and improve the reliability of the correlation of P to R.

Thus, for all these reasons, arterial blood pressure can be reliably estimated from aortic resistance using the general technique of FIG. 2. Turning now to the remaining figures, various exemplary embodiments will be described that are provided in accordance with the general technique of FIG. 2.

Exemplary Implementations

Figure 3:
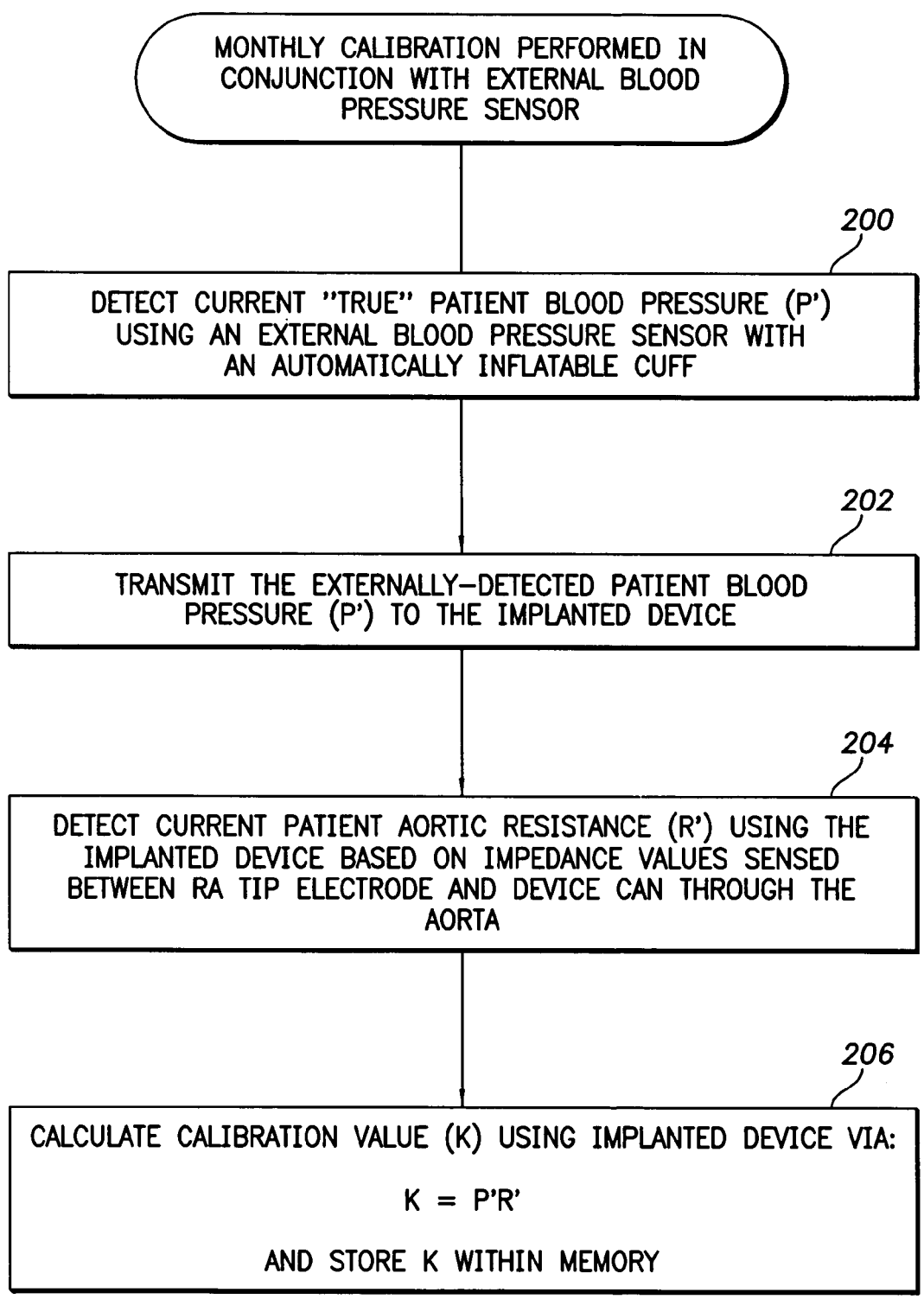
FIG. 3 illustrates an exemplary monthly calibration procedure for use in conjunction with the general blood pressure detection technique of FIG. 2.

FIG. 3 summarizes an exemplary calibration technique for calculating K, which may be performed, e.g. monthly. At step 200, an external blood pressure sensor (such as monitor 18 of FIG. 1), detects the current, "true" arterial blood pressure of the patient. For example, the patient may be instructed to use a bedside monitor with automatically inflating cuff to detect the arterial blood pressure. For systems that provide both systolic and diastolic pressures, these two values may be averaged to provide a single arterial blood pressure value (P'), which is transmitted to the pacer/ICD at step 202. In other embodiments, such as in FIG. 11, described below, both systolic and diastolic pressures are preferably transmitted to the pacer/ICD for use in calculating K. At step 204, the pacer/ICD detects the current patient aortic resistance (R') based on resistance values sensed between the RA tip electrode and the device can electrode, as described in connection with FIG. 3. Preferably, P' and R' are detected at substantially the same time. This may be achieved, e.g., by having the external device transmit the precise date/time at which it detected P' to the pacer/ICD. Meanwhile, the pacer/ICD detects R' at least once per heart beat and records the most recently detected R' values along with their date/time. This allows the pacer/ICD to then match P' with the contemporaneous R' value based on the respective date/time stamps. At step 206, the pacer/ICD calculates the calibration value (k) via:

$$K = P'R'$$

and stores K within memory, replacing any previously recorded K values. In some implementations, the external device is programmed to detect and transmit several P' values taken at somewhat different times (perhaps five minutes apart). The pacer/ICD retrieves the corresponding R' values for each of the P' values and then calculates separate, individual K values using each of the P', R' pairs. The pacer/ICD then averages the separate K values to yield a final K value for use in the subsequent detection of P using P=K/R. In other words, K is calculated as an average of several data points to improve accuracy. If a more complex correlation equation is employed, such as $P=K_2+K_3/R$, then multiple data points are used to permit calculation of the multiple coefficients (e.g. $K_2$, $K_3$) using otherwise conventional techniques.

Depending upon the circumstances, the external blood pressure sensor may be operated by the patient or, if unable to do so, by a nurse, physician or other clinician. The external blood pressure sensor may be, e.g., part of a bedside monitor for use in a home or hospital. In some examples, the external blood pressure sensor is an otherwise conventional blood pressure sensor modified to transmit the blood pressure information (i.e. P' values) to the pacer/ICD. In other examples, the external blood pressure sensor is part of a programmer device capable of actually programming operations of the pacer/ICD as well as capable of receiving and displaying a wide range of diagnostic information received from the pacer/ICD, such as IEGM data, etc. As will be explained in connection with FIGS. 6 and 7, the external blood pressure sensor may also be equipped to detect systemic resistance ($R_a$) for use in stroke volume determination.

Figure 4:
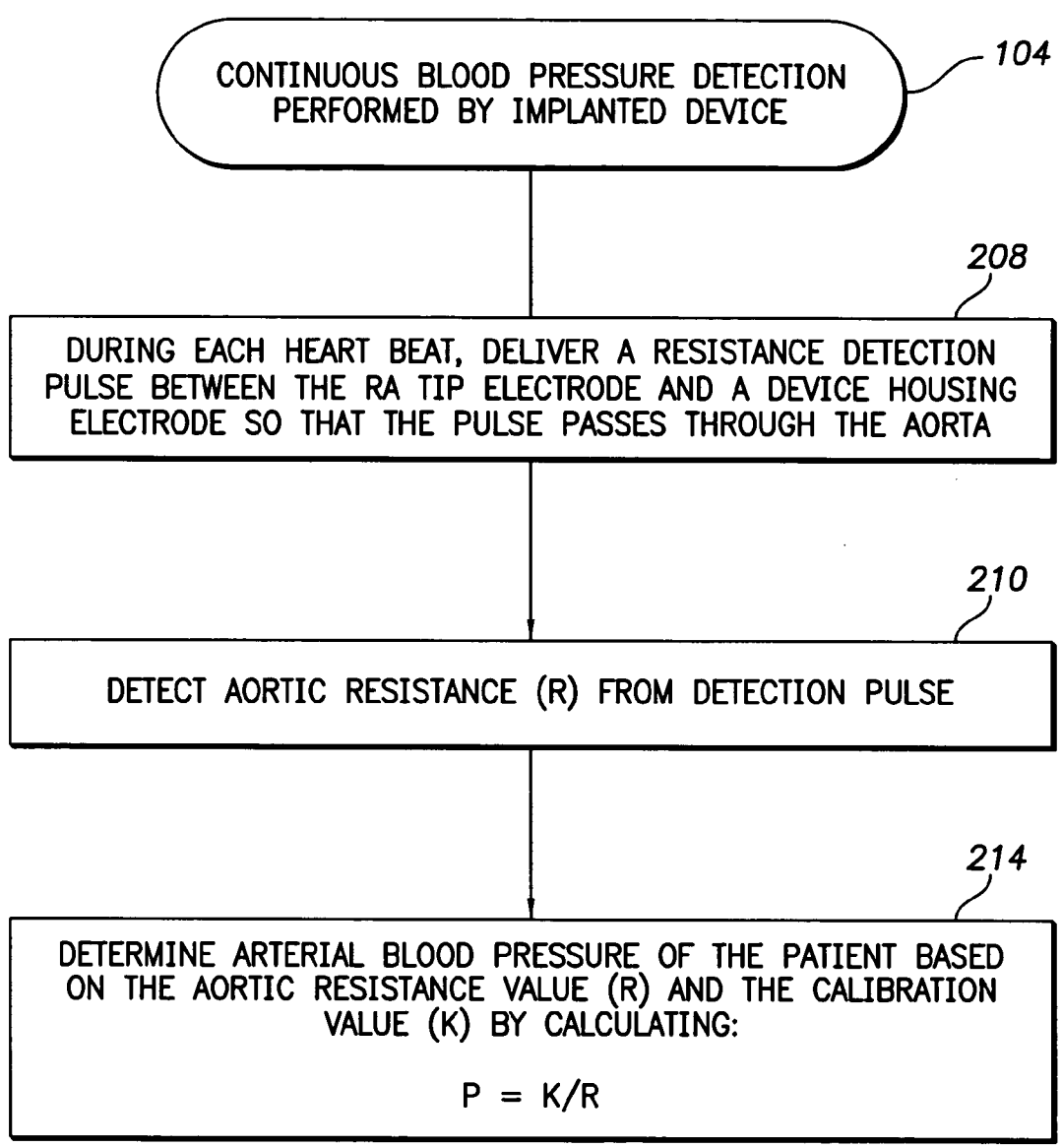
FIG. 4 illustrates an exemplary continuous blood pressure detection technique for use in conjunction with the general blood pressure detection technique of FIG. 2.

Turning now to FIG. 4, an exemplary technique for using the calibration value K generating via the technique of FIG. 3 to calculate P will now be described. During each heartbeat, at step 208, the pacer/ICD delivers a resistance detection pulse between the RA tip electrode and device housing so that the pulse passes along a current vector through the aorta. At step 210, the pacer/ICD detects the resulting resistance value, which is used as the aortic resistance (R). At step 214, the pacer/ICD determined the arterial blood pressure (P) of the patient based on the aortic resistance value (R) and the calibration value (K) by calculating: P=K/R. If a more complex correlation formula is used, such as P=$K_2$+$K_3$/R, then P is instead calculated using the more complex formula with the appropriate calibration coefficients.

Hence, FIG. 4 illustrates an example of an arterial blood pressure detection technique that may be performed in accordance with step 104 of FIG. 2. Preferably, the technique of FIG. 4 is performed at least once per cardiac cycle to thereby substantially continuously detect arterial pressure (P). However, the procedure may instead be performed more or less frequently. At least some of the individual pressure data values, thus calculated, are stored in device memory for subsequent review. In some implementations, all pressure values detected over a one day period are averaged and stored so that the average blood pressure of the patient may be tracked from day to day. In some implementations, any abnormally high or low individual blood pressure values may be stored for review.

Figure 5:
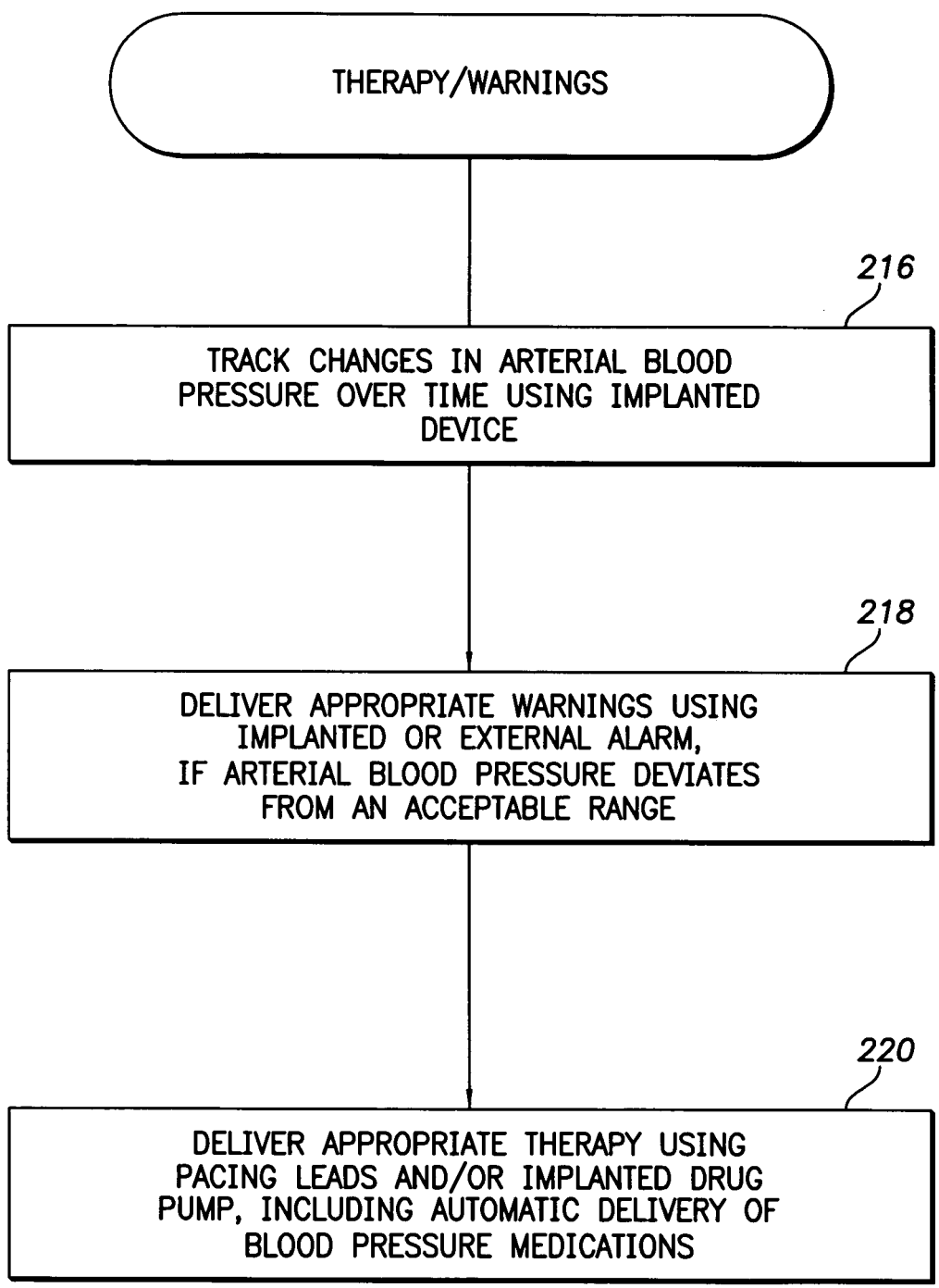
FIG. 5 illustrates an exemplary therapy delivery technique for use in addition to the general blood pressure detection technique of FIG. 2.

FIG. 5 summarizes therapy and warning signals that may be controlled in response to the blood pressure values detected by the technique of FIG. 4. At step 216, the pacer/ICD tracks changes in arterial blood pressure over time, such as by recording a daily blood pressure average. At step 218, the pacer/ICD delivers appropriate warnings (using, e.g., implanted alarm 20 of FIG. 1) if the blood pressure deviates from predetermined acceptable range. In other words, if the blood pressure becomes either too high or too low, appropriate warnings are generated. The warnings may differ from one another so that the patient can distinguish therebetween. If the pacer/ICD is equipped to operate in conjunction with a bedside monitor, any warning signals may also be transmitted to the bedside monitor for conversion into audible and/or visible warnings. The warnings may be forwarded, if warranted, from the bedside monitor to a nurse or physician.

At step 220, appropriate therapy is automatically delivered using, e.g., implanted drug pump 22 of FIG. 1. The specific therapy depends on the particular blood pressure problem. If a sustained increase in blood pressure is detected, appropriate blood pressure reduction medications may be automatically delivered by the implanted device, if it is so equipped. Pacing therapy may be automatically adjusted as well. For example, it may be appropriate to discontinue overdrive pacing in response to abnormally high blood pressure. If a short-term drop if blood pressure is detected, the heart may be temporarily paced at a higher rate so as to increase the blood pressure. As can be appreciated, a wide variety of other therapies and/or medications can be delivered or controlled in response to blood pressure problems and no attempt is made herein to describe all such responses.

Figure 6:
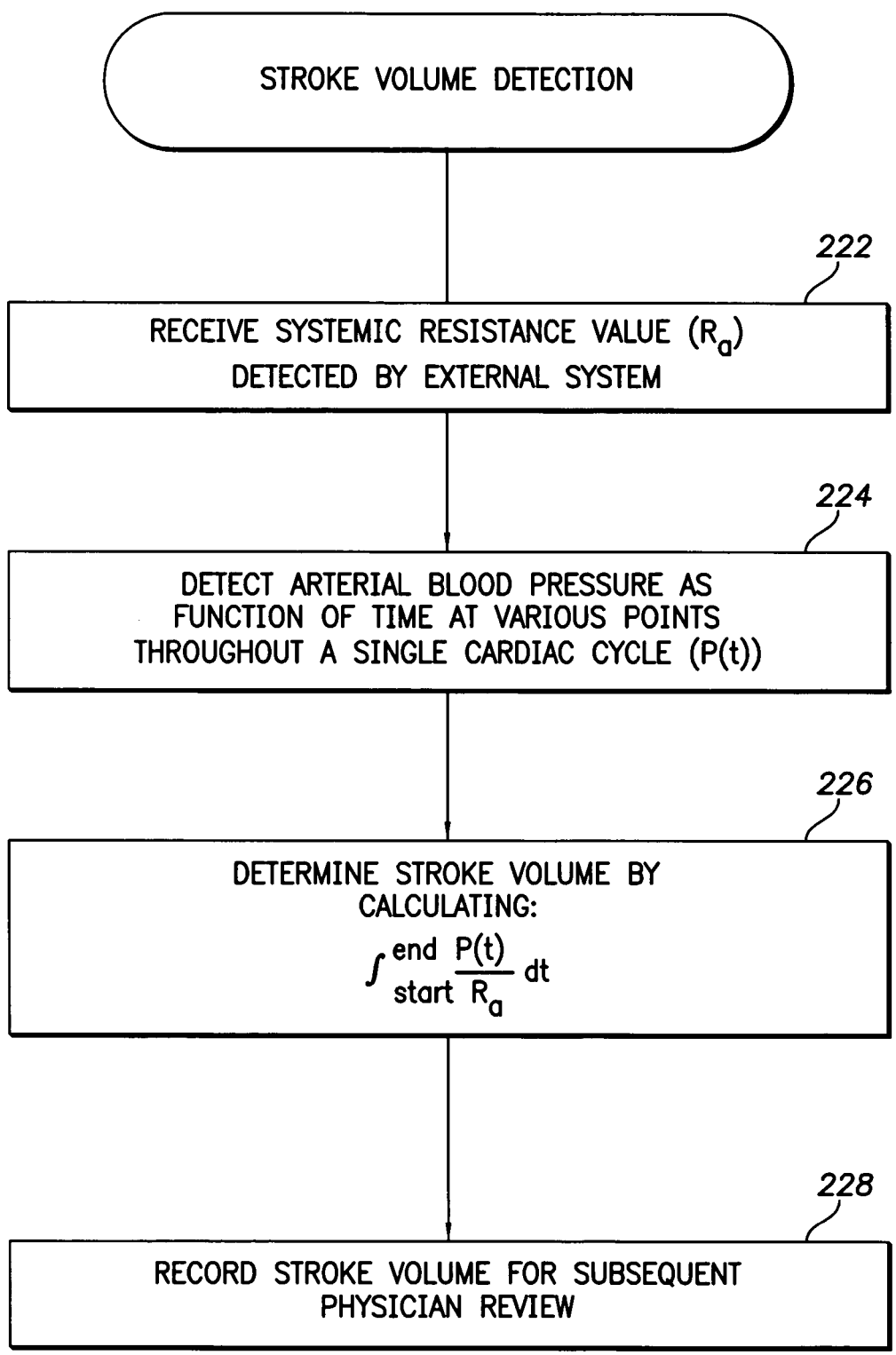
FIG. 6 illustrates an exemplary stroke volume detection technique for use in addition to the general blood pressure detection technique of FIG. 2 wherein stroke volume is calculated in conjunction with a single systemic resistance value detected using an external system.
Figure 7:
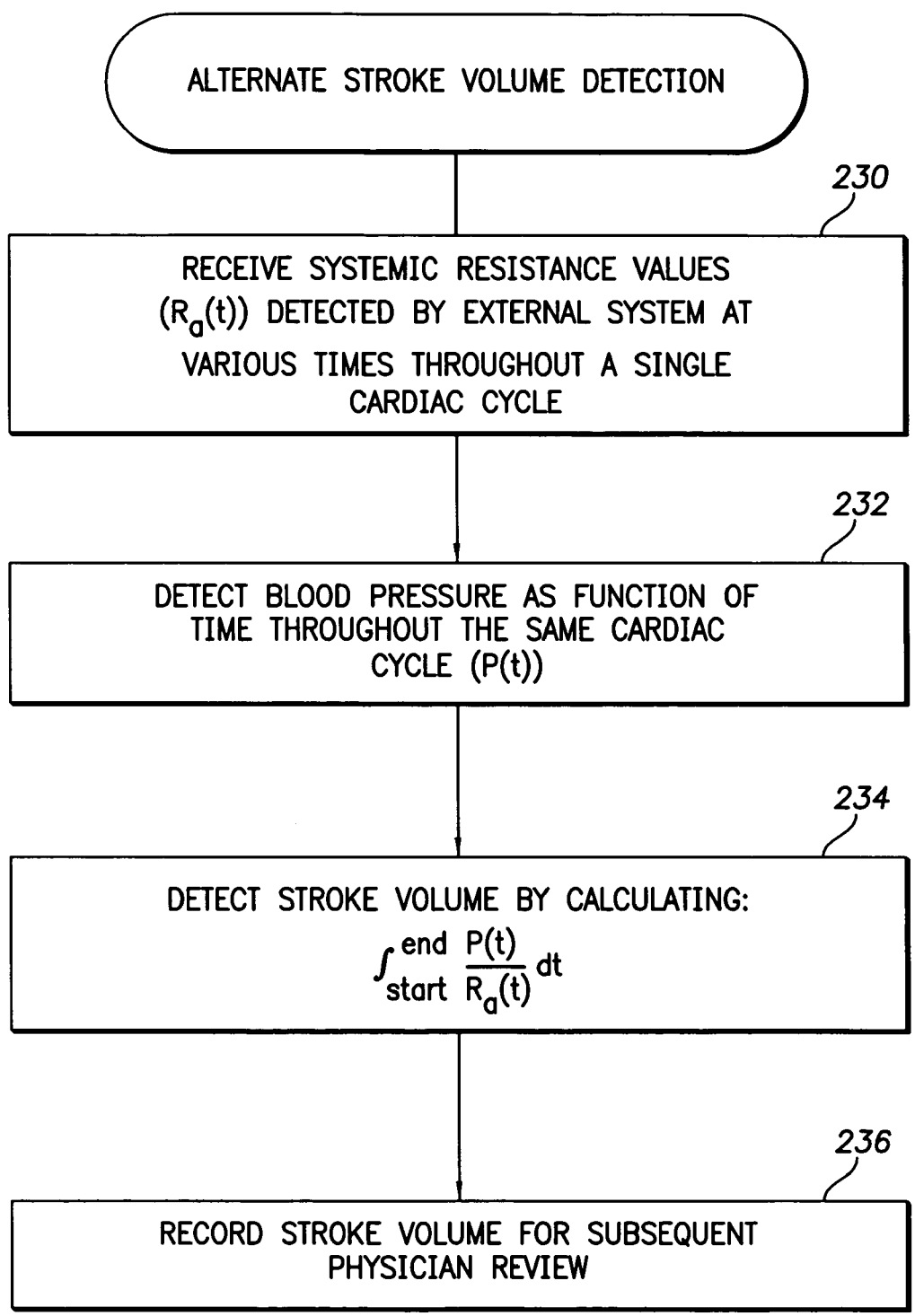
FIG. 7 illustrates an alternative stroke volume detection technique for use instead of the stroke volume detection technique of FIG. 6 wherein stroke volume is calculated in conjunction with a series of systemic resistance values also detected using an external system.

Turning now to FIGS. 6 and 7, exemplary techniques for detecting stroke volume using internally detected arterial pressure values (P) in conjunction with externally derived systemic resistance value (Ra) will now be described. In the technique of FIG. 6, a single systemic resistance value (Ra) is used in conjunction with a plurality of pressure values detected during a single cardiac cycle. In the technique of FIG. 7, multiple systemic resistance values (Ra) are used, also in conjunction with a plurality of pressure values.

Briefly, stroke volume can be derived from arterial pressure and systemic (aortic or arterial) resistance as follows. For electrical circuits, Ohm's law states that current is equal to voltage divided by resistance. The hemodynamic equivalent is: Flow=Pressure÷Resistance. Assume that an external system determines the arterial tree resistance of the patient (Ra) in units of ls-1 mmHg-1 or liters per second per mmHg of pressure. Then the instantaneous hemodynamic flow is given by: F=P/Ra. Stroke volume can then be derived by integrating the instantaneous flow over a single cardiac cycle as follows:

$$\text{Stroke volume} = \int_{start}^{end} \frac{P(t)}{R_a} dt$$

where P(t) represents arterial blood pressure as a function of time through the single cardiac cycle, $R_a$ represents the externally derived systemic resistance, "start" represents the time at the start of the cardiac cycle and "end" represents the time at the end of the cardiac cycle.

Within FIG. 6, beginning at step 222, the pacer/ICD receives a systemic resistance value ($R_a$) detected using an external system, such as the DynaPulse® system of Pulse Metric, Inc. of San Diego, Calif., modified as needed to transmit the systemic resistance value ($R_a$) to the pacer/ICD. At step 224, the pacer/ICD detects a plurality of values of arterial pressure (P) during a single cardiac cycle using the techniques of FIG. 4, i.e. the pacer/ICD detects arterial blood pressure as a function of time P(t) during the cardiac cycle. For example, several dozen pressure values may be detected during a single cardiac cycle beginning at time "start" and ending at time "end." Preferably, the systemic resistance value ($R_a$) is detected during the same cardiac cycle or at least at about the same time.

At step 226, the pacer/ICD then calculates stroke volume using a discrete version of:

$$\text{Stroke volume} = \int_{start}^{end} \frac{P(t)}{R_a} dt.$$

That is, the above integral equation is internally calculated within the pacer/ICD as a discrete sum rather than as a continuous integral, using individual values of P(i=1, 2, . . . n) detected during the interval between the start time and the end time. Multiple individual stoke volume values may be calculated for separate cardiac cycles, then averaged to yield an average stroke volume, which may be recorded by the pacer/ICD at step 228 for subsequent review. The stroke volume values may also be used to trigger or controller therapy and warning signals if stroke volume is found to deviate from predetermined acceptable bounds.

Within FIG. 7, beginning at step 230, the pacer/ICD receives a plurality of systemic (arterial or aortic) resistance values ($R_a$(t)) detected using the external system over the course of a single cardiac cycle. At step 232, the pacer/ICD detects a plurality of values of arterial pressure (P) during the same cardiac cycle, again using the techniques of FIG. 4. Care is taken to ensure that the detection times for the individual systemic resistance values are substantially the same as the detection times of the individual arterial pressure values. This may be achieved by date/time stamping the various individual values. At step 234, the pacer/ICD then calculates stroke volume using a discrete version of:

$$\text{Stroke volume} = \int_{start}^{end} \frac{P(t)}{R_a(t)} dt$$

As above, the integral equation is internally calculated within the pacer/ICD as a discrete sum rather than as a continuous integral. Again, multiple individual stoke volume values may be calculated for separate cardiac cycles, then averaged to yield an average stroke volume for storage by the pacer/ICD at step 228.

Thus, FIGS. 6 and 7 illustrate techniques for calculating stroke volume based on arterial pressure and a systemic resistance value derived from an external monitor. Often, such monitors are available in hospitals and physician offices. Once the pacer/ICD calculates stroke volume, it transmits the value to the external monitor (or to another external device) for display. This allows a physician or other clinician to easily obtain an estimate of stroke volume using only the systemic resistance monitor and the pacer/ICD without requiring other, more complicated external stroke volume detection systems. Alternatively, rather than configure the pacer/ICD to calculate stroke volume, the pacer/ICD instead transmits the arterial blood pressure values (i.e. P(t)) to the external device, which performs the actual calculation. Yet alternatively, if the implanted system is equipped to estimate systemic resistance itself, then an external system resistance monitor is not required and the pacer/ICD can detect stroke volume substantially continuously. In this regard, a measure of systemic resistance may be estimated by the implanted device itself based on a combination of a pressure measurement (either derived using the techniques described above or derived using an otherwise conventional implantable blood pressure sensor) and a measure of cardiac output (derived by the implanted device via some other technique than that set forth in FIG. 8.) See, for example, techniques set forth in U.S. Pat. No. 6,314,323 to Ekwall, entitled "Heart Stimulator Determining Cardiac Output, by Measuring The Systolic Pressure, for Controlling The Stimulation" See also techniques set forth in U.S. patent application Ser. No. 11/099,888, filed Apr. 5, 2005, entitled "System and Method For Measuring Cardiac Output Via Thermal Dilution using an Implantable Medical Device with an External Ultrasound Power delivery System."

Figure 8:
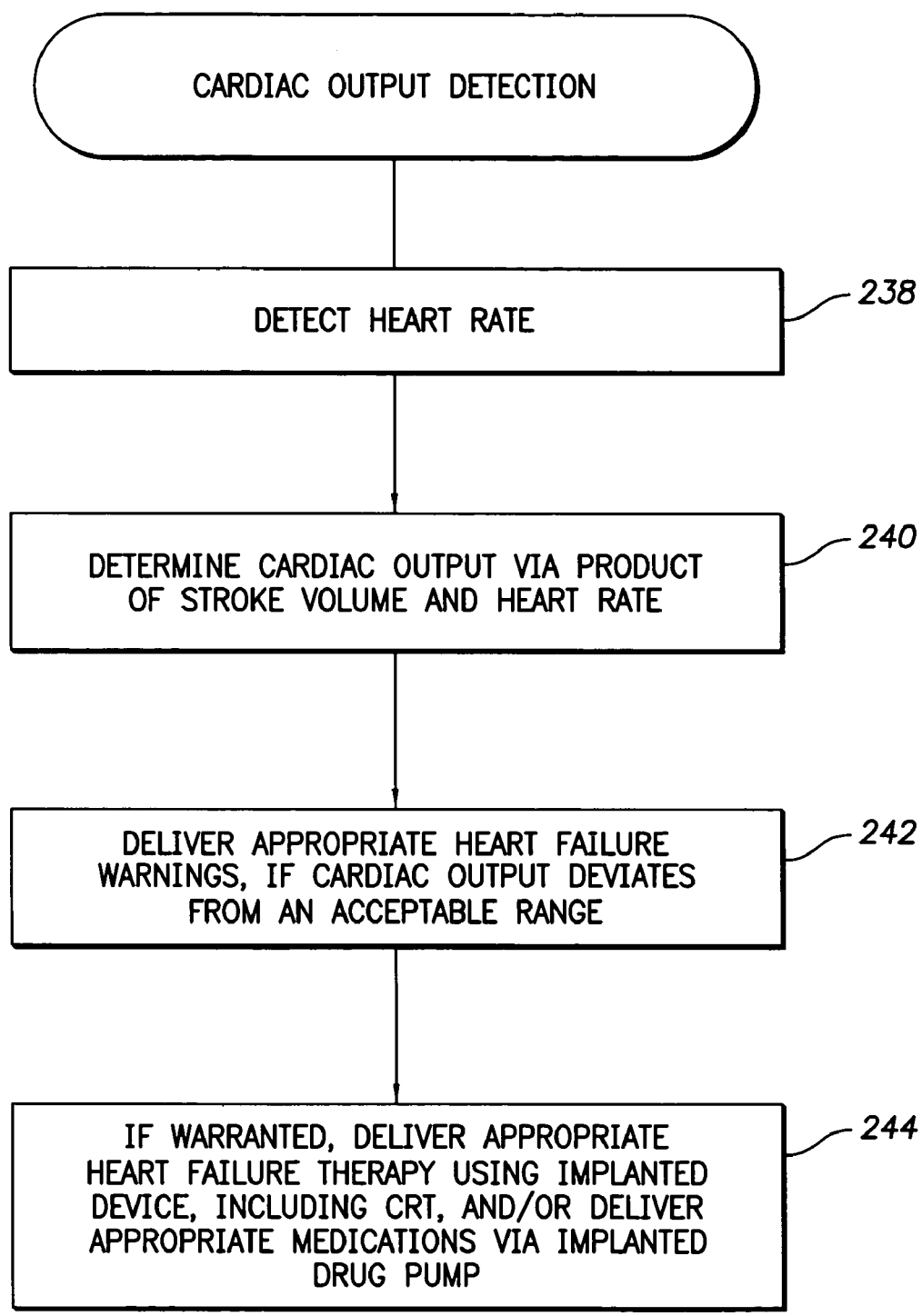
FIG. 8 illustrates an exemplary cardiac output detection technique for use in addition to the stroke volume detection technique of FIG. 6 or 7.

FIG. 8 summarizes a cardiac output detection technique that utilizes the stroke volume detected via FIGS. 6 and 7. This technique may be used, e.g., in implementations that do not have other cardiac output detection capabilities, such as those cited immediately above. Alternatively, the technique may be used in implementations that have other cardiac output detection capabilities so as to confirm the cardiac output measurement. At step 238, the pacer/ICD detects patient heart rate using, for example, IEGM signals. At step 240, the pacer/ICD determines cardiac output as the product of stroke volume and heart rate. At step 242, the pacer/ICD compares the cardiac output against predetermined acceptable thresholds indicative of possible CHF and generates and delivers appropriate warnings if the cardiac output deviates from an acceptable range. At step 244, the pacer/ICD also delivers appropriate heart failure therapy, if warranted. Depending upon the implementation, the pacer/ICD may be equipped to deliver CRT. Additionally, or alternatively, the implanted drug pump may deliver medications appropriate for use with heart failure. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure.

Hence, an accurate cardiac output can be advantageously determined using this technique whenever stroke volume is accurately determined in conjunction with the aforementioned external systemic resistance monitor. This allows a physician or other clinician to easily obtain an estimate of cardiac output without requiring other, more complicated external cardiac output detection systems. Alternatively, rather than configuring the pacer/ICD to calculate cardiac output, the pacer/ICD instead transmits arterial blood pressure values (i.e. P(t)) to the external systemic resistance monitor along with the heart rate, which performs the actual calculation of cardiac output. Yet alternatively, if the implanted system is equipped to determine systemic resistance itself, then an external system resistance monitor is not required and the pacer/ICD can directly and more frequently detect both stroke volume and cardiac output.

Figure 9:
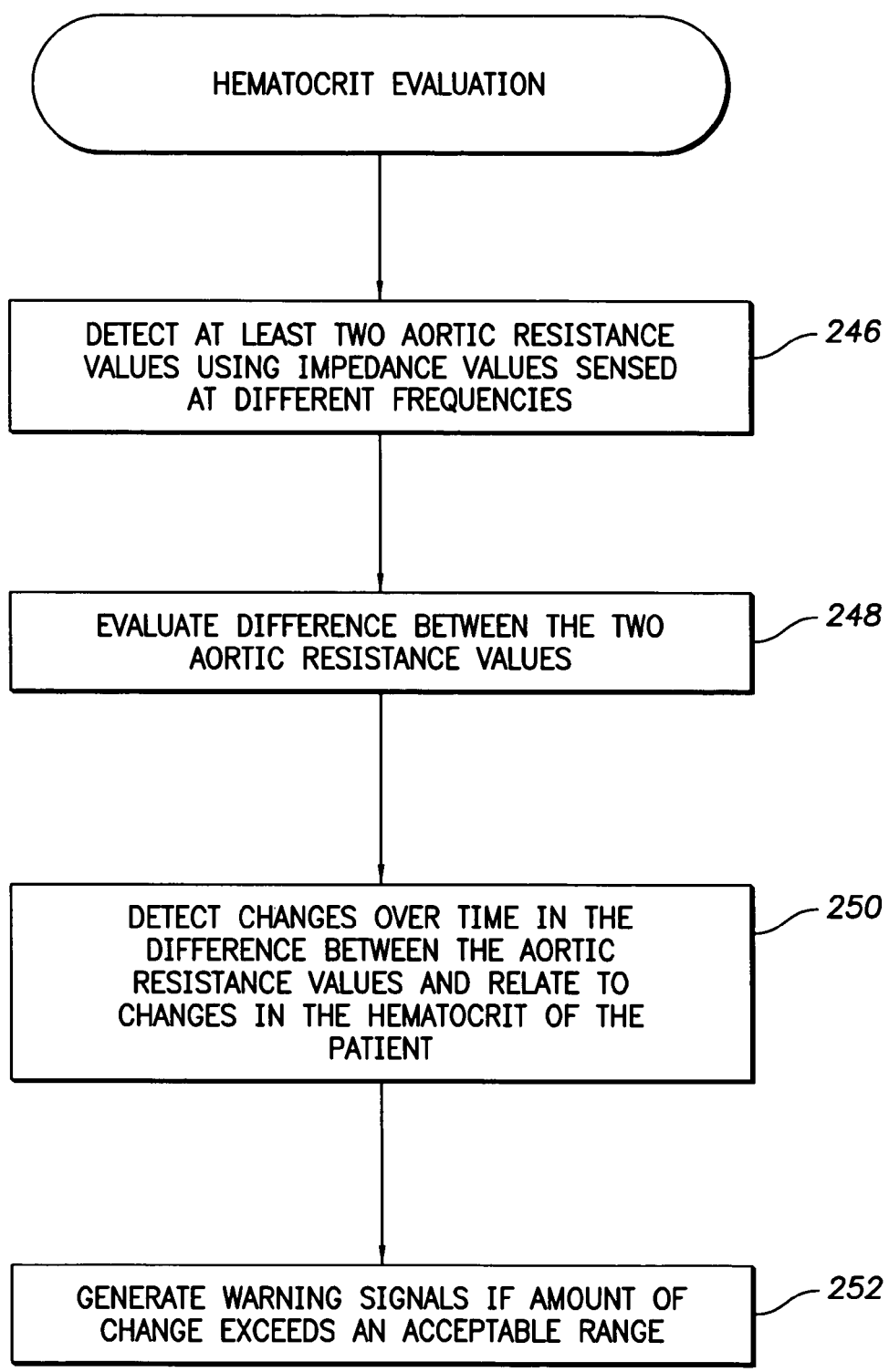
FIG. 9 illustrates an exemplary hematocrit evaluation technique for use in addition to the general blood pressure detection technique of FIG. 2.

FIG. 9 summarizes a hematocrit evaluation technique that may be performed by the pacer/ICD of FIG. 1. Briefly, aortic resistance is affected by the hematocrit since red cells are good insulators at low frequencies. However, for frequencies above about 5 kHz, the red cells short out capacitively and the resistance is thus not affected by the hematocrit. Hence, as noted above, arterial pressure is preferably determined using aortic resistance values detected at a frequency greater than 5 kHz so that changes in hematocrit do not affect the determination of arterial pressure. By additionally detecting aortic resistance at a lower frequency, the pacer/ICD can also provide information indicative of any significant changes in hematocrit. Briefly, beginning at step 246, the pacer/ICD detects at least two aortic resistance values at different frequencies. This may be achieved by delivered two separate resistance detection pulses between the RA tip and the device housing at two separate frequencies. Alternatively, depending upon the characteristics of the resistance detection pulse, the two separate resistance value can be derived from a single detection pulse. In any case, preferably, a first aortic resistance value is detected at a frequency in the range of 100 to 1 kHz. A second aortic resistance value is detested at a higher frequency in the range of 10 to 100 kHz. At step 248, the pacer/ICD evaluates the difference between the two resistance values by, for example, subtracting one from the other, and then stores the difference value. At step 250, the pacer/ICD detects any changes over time in the difference value and relates the changes to changes in the hematocrit of the patient. That is, an increase in the difference value is indicative of an increase in hematocrit, i.e. a greater proportion, by volume, of patient blood now consists of red blood cells; whereas decrease is indicative of a decrease in hematocrit.

Changes over time in hematocrit may be detected by periodically storing the differences values then comparing the latest difference value with predecessor difference values. At step 252, the amount of any change in the difference values is compared against predetermined thresholds and appropriate warnings are delivered if hematocrit appears to deviate from acceptable bounds. For example, if the change in difference values is indicative of at least a 10% decrease in hematocrit, warnings are generated. Note that the technique of FIG. 9 does not quantify the hematocrit, rather the technique detects changes in hematocrit. Alternatively, the pacer/ICD may be configured to actually estimate the hematocrit of the patient using externally-derived hematocrit calibration values.

Figure 10:
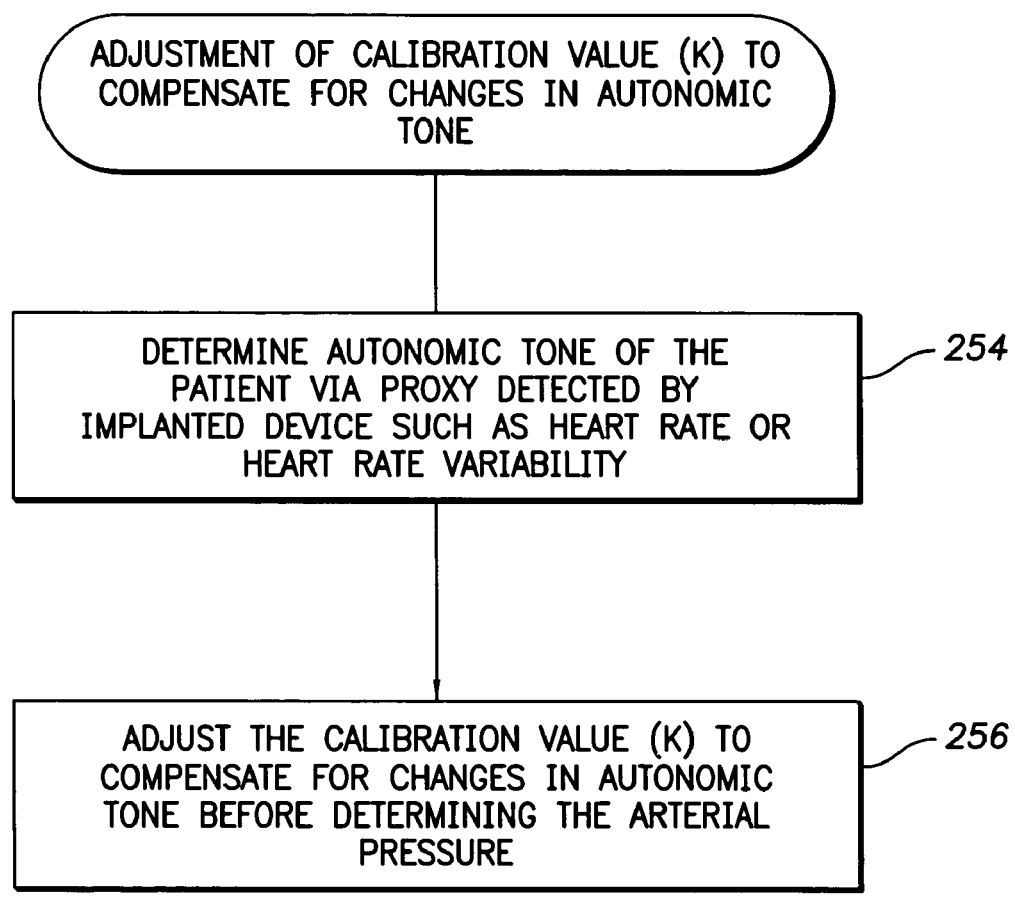
FIG. 10 illustrates an exemplary autonomic tone-based recalibration technique for use in addition to the monthly calibration technique of FIG. 3.

Turning now to FIG. 10, a technique for adjusting the calibration value (K) between monthly calibration sessions to account for variations in autonomic tone will now be described. Briefly, autonomic tone can affect the determination of arterial pressure because aortic compliance is affected by autonomic tone. That is, an increase in autonomic tone can make the aorta less compliant thus decreasing the extent to which the aorta distends in response to an increase in blood pressure. Beginning at step 254, the pacer/ICD detects a value representative of the autonomic tone of the patient. This may be achieved, e.g., by detecting any of a variety of proxies for autonomic tone, such as heart rate, heart rate variability and/or direct measures of sympathetic electrical activity sensed using implanted neural sensors. At step 256, the pacer/ICD then adjusts the calibration value (K) to compensate for changes in autonomic tone before determining the arterial pressure from the aortic resistance via the general technique of FIG. 2. In one example, a 10% increase in heart rate is deemed indicative of a 10% increase in autonomic tone and so the calibration factor is likewise changed by 10% to compensate.

Figure 11:
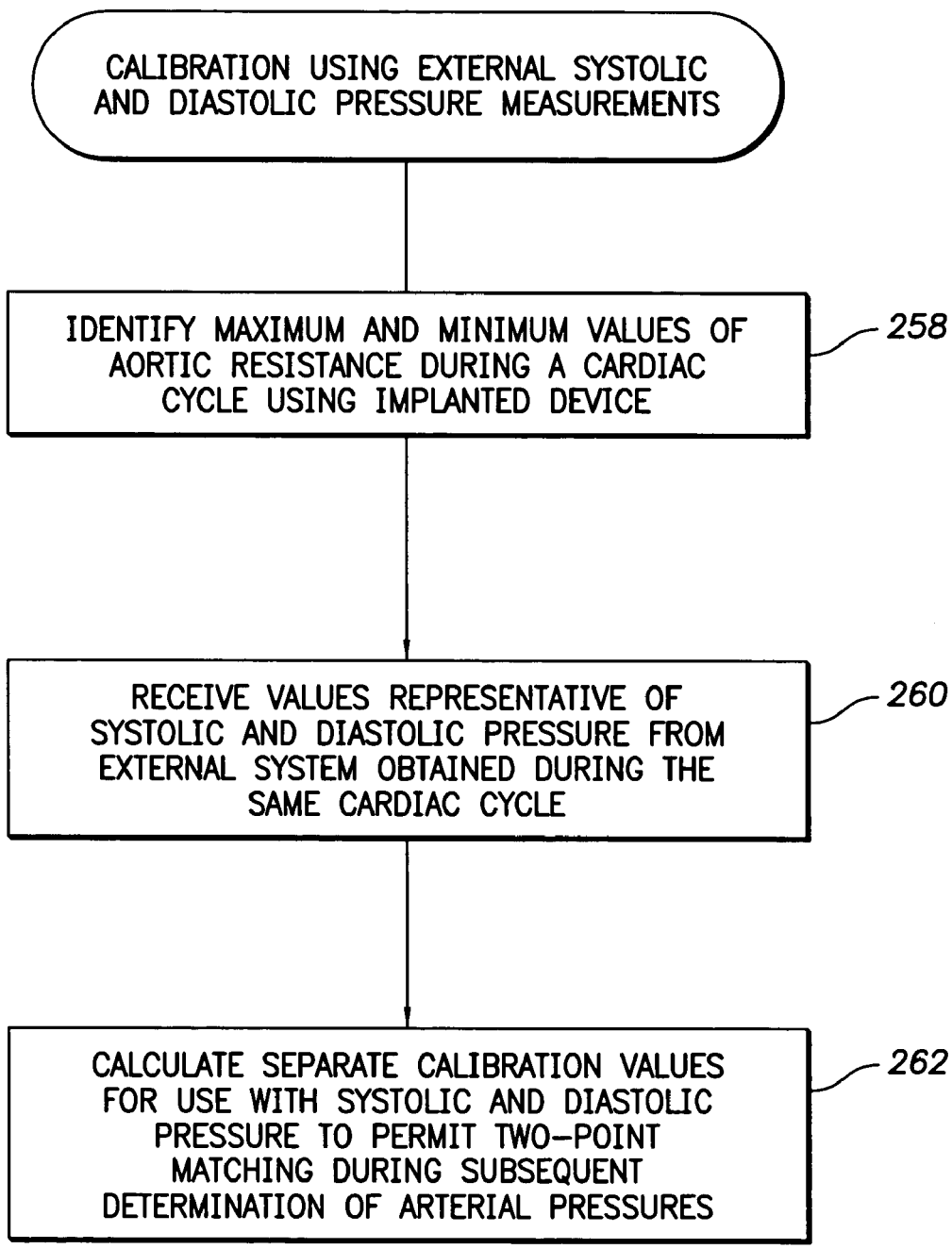
FIG. 11 illustrates an exemplary systolic/diastolic-based recalibration technique for use in addition to the monthly calibration technique of FIG. 3.

FIG. 11 summarizes a technique for determining arterial pressure while taking into account both systolic and diastolic blood pressure measurements. The calibration technique described above in connection with FIG. 3 utilizes an average arterial pressure (P') derived from an external system to calculate a single calibration value (K). In contrast, with the technique of FIG. 11, separate systolic and diastolic pressure measurements ($P'_{systolic}$, $P'_{diastolic}$) are used to calculate separate calibration factors ($K_{systolic}$, $K_{diastolic}$). Beginning at step 258, the pacer/ICD identifies maximum and minimum values of aortic resistance (R) during a single cardiac cycle. At step 260, the pacer/ICD receives separate values representative of systolic and diastolic pressure ($P'_{systolic}$, $P'_{diastolic}$) from the external blood pressure sensor derived during the same cardiac cycle. At step 262, the pacer/ICD calculates and stores the calibration values ($K_{systolic}$, $K_{diastolic}$). Thereafter, the pacer/ICD can determine the systolic and diastolic arterial pressure ($P_{systolic}$, $P_{diastolic}$) by detecting and recording the maximum and minimum aortic resistances during a given cardiac cycle. Moreover, the pacer/ICD can also perform two-point matching to more precisely calculate pressure values between systolic and diastolic. That is, for any aortic resistance value detected between the systolic and diastolic phases of a cardiac cycle, the pacer/ICD can more precisely calculate the corresponding arterial pressure by scaling between the systolic and diastolic pressures ($P_{systolic}$, $P_{diastolic}$).

In the following sections, exemplary pacer/ICDs will be described, which include components for performing the above-described techniques.

Exemplary Pacer/ICD

Figure 12:
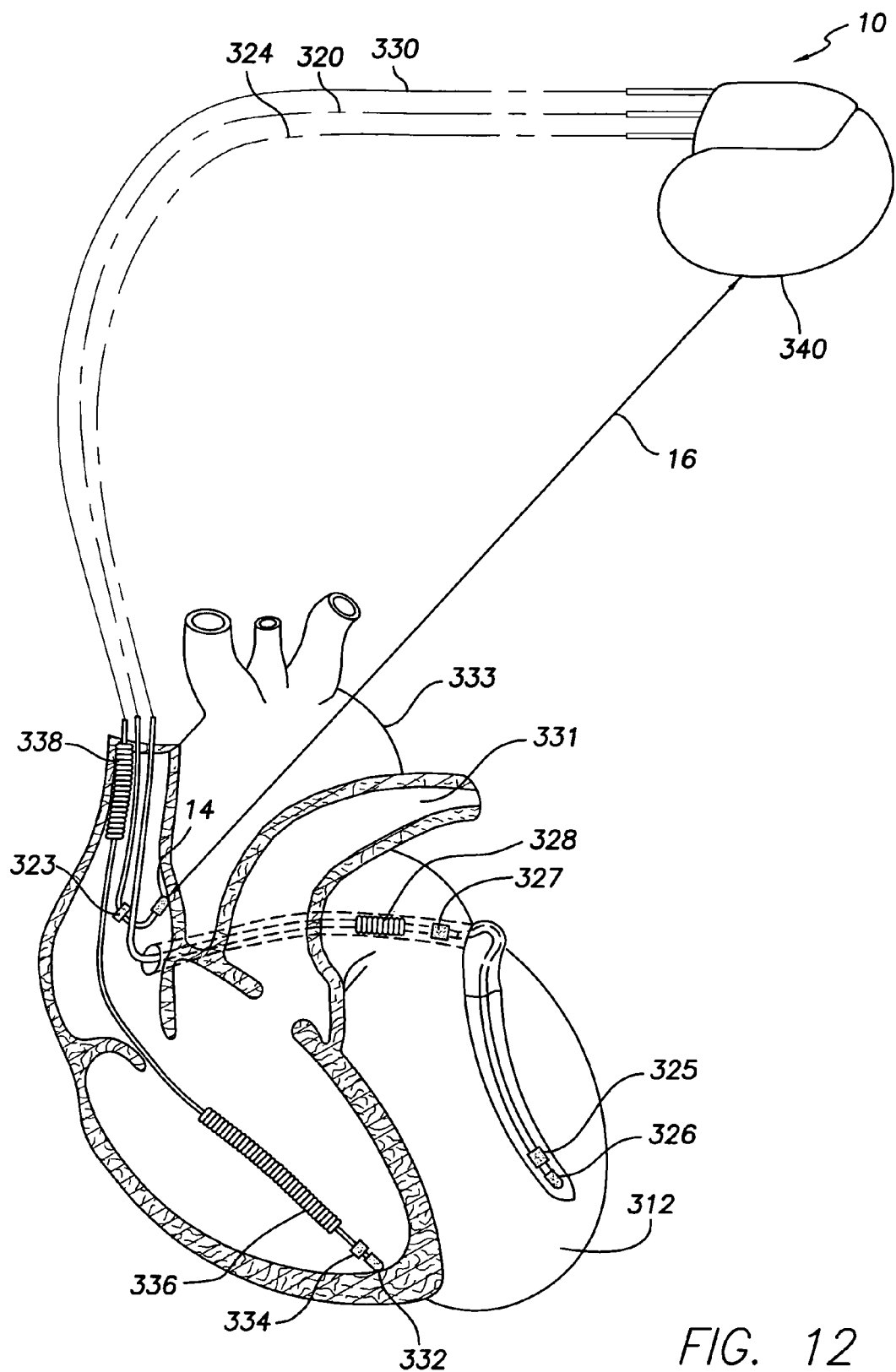
FIG. 12 illustrates an implementation of the implantable system of FIG. 1 wherein the pacer/ICD is positioned such that the aortic arch of the patient is between an RA electrode and the device housing.

FIG. 12 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of determining arterial blood pressure and related physiological parameters, such as cardiac output, and controlling the delivery of therapy and warnings in response thereto. To provide atrial chamber pacing stimulation and sensing, pacer/ICD 10 is shown in electrical communication with a heart 312 by way of a right atrial lead 320 having a right atrial (RA) tip electrode 14 and an RA atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus as for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 12, it should also be understood that additional stimulation leads (with one or more pacing, sensing and/or shocking electrodes) may be used in order to efficiently and effectively provide pacing stimulation to the left side of the heart or atrial cardioversion and/or defibrillation.

As may be noted in FIG. 12, an electrical current path 16 may be established between RA atrial tip electrode 14 and the device case 340 for use in detecting resistance. (The return path of the current is via the RA lead 320.) Current path 16 passes directly through the aortic arch 333 of the heart, assuming the pacer/ICD is properly positioned. The typical implant location of a pacer/ICD is usually sufficient to place the aortic arch between the RA tip electrode and the device can, as shown in FIG. 12. If needed, though, the implant location for the pacer/ICD can be specifically chosen so that the aortic arch is located between the right atrial electrodes and the device can. (Note that FIG. 1, discussed above, does not necessarily show the pacer/ICD in its true relation to the heart.) The arrangement of FIG. 12 permits an accurate measure of aortic resistance for use in calculating arterial pressure, stroke volume, cardiac output, etc., as had already been described. In one specific example, RA tip electrode 14 and case 340 are employed to establish a current path; whereas RA ring electrode 323 and the device case 340 are employed to establish a separate voltage sensing vector.

Figure 13:
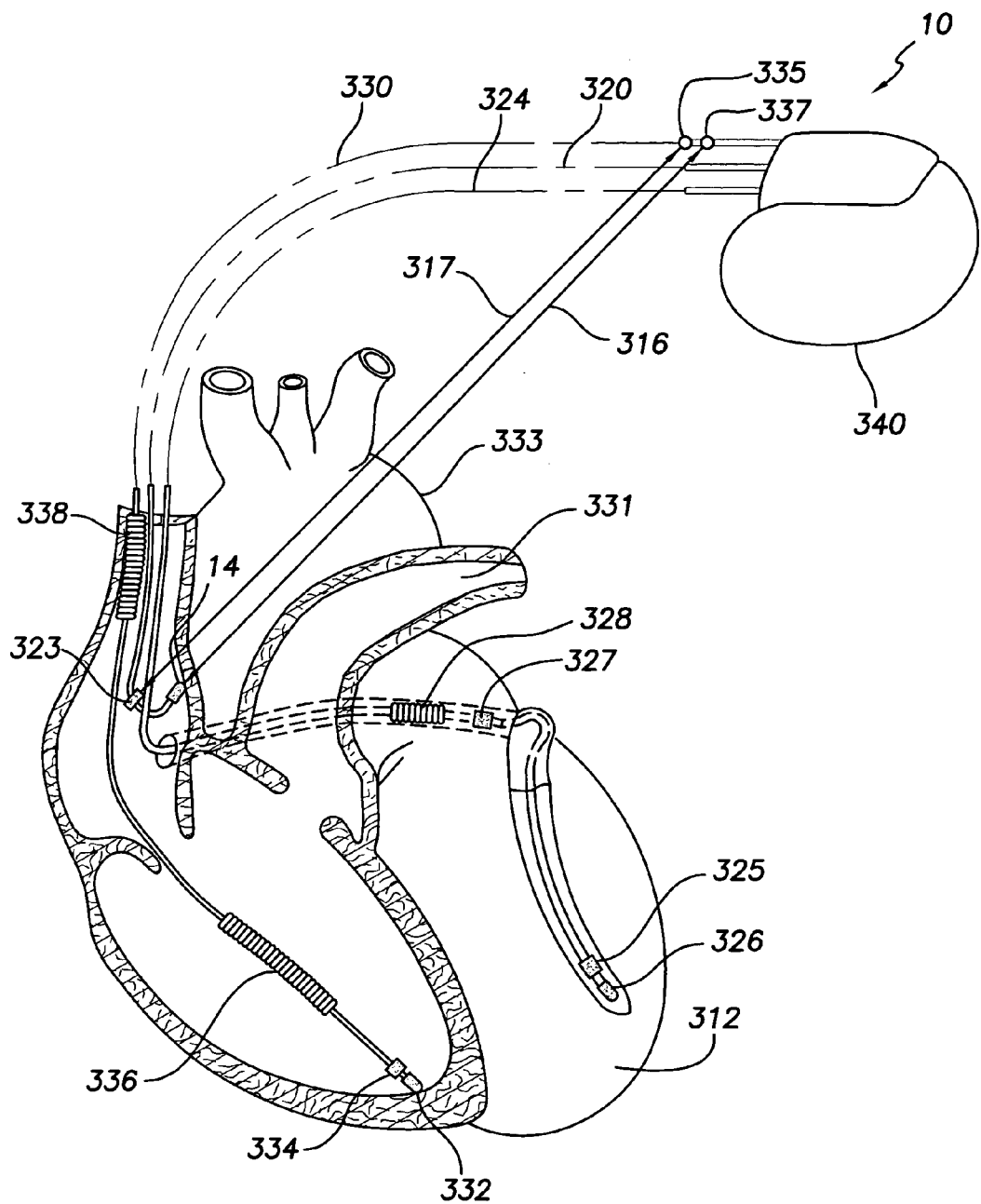
FIG. 13 illustrates an alternative implementation of the implantable system of FIG. 12, wherein the pacer/ICD is positioned such that the aortic arch of the patient is between the RA electrode and an additional sensing electrode mounted along the RV lead.

FIG. 13 shows an alternative embodiment. Here it may be seen that two electrode pairs, one in the heart and the other outside of the heart, are used for aortic resistance measurement. The first electrode pair includes electrodes 323 and 14, previously described. The second electrode pair includes electrodes 335 and 337, which are carried on lead 330. The electrodes 335 and 337 are carried high on the lead 330 so that they are on the side of the aortic arch 15 opposite electrodes 323 and 14 and the resulting vectors 316 and 317 for current establishment and voltage sensing pass through the aortic arch 333. The use of the second pair of electrodes allows the pacer/ICD to be positioned at a location off axis from the vectors, while still permitting the vectors to pass through aortic arch.

Figure 14:
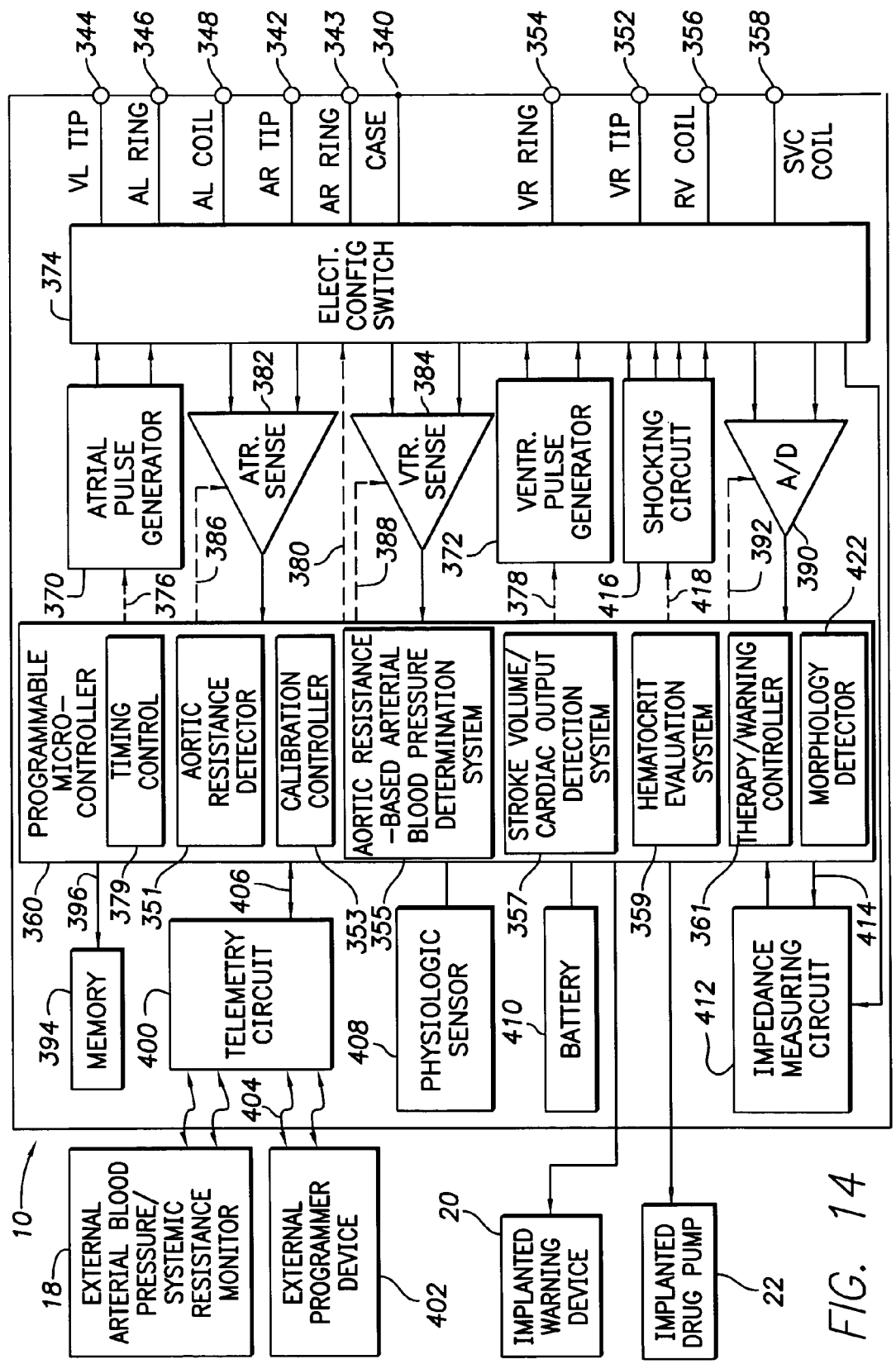
FIG. 14 is a functional block diagram of the pacer/ICD of FIG. 12 or 13, illustrating basic circuit elements that provide cardioversion, defibrillation and/or pacing stimulation in the heart and particularly illustrating components for detecting arterial blood pressure and related physiological parameters using the aortic resistance-based techniques of FIGS. 2-11.

A simplified block diagram of internal components of pacer/ICD 10 is shown in FIG. 14. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 340 for pacer/ICD 10, shown schematically in FIG. 14, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 14 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively. Although not shown, additional terminals may be provided to accommodate electrodes 335 and 337 of FIG. 13.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 14, an atrial pulse generator 370 and a ventricular/resistance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control, if provided, enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 14. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 14, pacer/ICD 10 is shown as having an resistance measuring circuit 412 which is enabled by the microcontroller 360 via a control signal 414. Herein, resistance is primarily detected for use in detecting aortic resistance. Other uses for an resistance measuring circuit include, but are not limited to, lead resistance surveillance during the acute and chronic phases for proper lead positioning or dislodgement; detecting operable electrodes and automatically switching to an operable pair if dislodgement occurs; measuring respiration or minute ventilation; measuring thoracic resistance for determining shock thresholds; detecting when the device has been implanted; measuring stroke volume; and detecting the opening of heart valves, etc. The resistance measuring circuit 120 is advantageously coupled to the switch 74 so that any desired electrode may be used.

If pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level and pertain to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to detecting arterial blood pressure and related physiological parameters. In particular, an aortic resistance detector 351 operates to detect aortic resistance values (R) from resistance values obtained by resistance sensing circuit 412. A calibration controller 353 periodically calculates calibration values (K), using the techniques described above primarily in connection with FIG. 3, based on the aortic resistance values (R') detected by resistance detector 351 and true blood pressure values (P') received from an external blood pressure monitor 18, via telemetry circuit 400. An aortic resistance-based arterial blood pressure determination system 355 then determines arterial pressure (P), substantially continuously, from newly detected aortic resistance values (R) using the techniques described above primarily in connection with FIG. 4. A stroke volume/cardiac output detection system 357 estimates stroke volume and cardiac output using the techniques described above primarily in connection with FIGS. 6-8, based on systemic resistance values received from monitor 18. A hematocrit evaluation system 350 evaluates changes in the hematocrit of the patient using the techniques described above primarily in connection with FIG. 9. Therapy and/or warnings are generated and controlled by therapy/warning controller 361. Drug therapy may be delivered via implanted drug pump 22. Warnings maybe delivered via implanted warning device 20 and/or relayed to external monitor 16. Connection terminals for coupling the pacer/ICD to the drug pump and implanted warning device are not separately shown. Instead, for clarity and simplicity, the drug pump and warning device are shown as being functionally connected directly to the microcontroller.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

What have been described are techniques and systems for determining arterial blood pressure and related physiological parameters and for detecting and evaluating heart failure and other medical conditions. Principles of the invention may be exploiting using other implantable systems or in accordance with other techniques. Indeed, general principles invention may be exploited with systems not incorporating pacemakers or ICDs but instead incorporating other implantable medical devices. As can be appreciated, a wide variety of specific implementations may be developed consistent with the principles of the invention and no attempt is made herein to describe or enumerate all such possible implementations. Thus, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for detecting blood pressure, the method comprising:
   detecting a value representative of aortic electrical resistance (R) within the patient using a detector; and
   in the implantable medical device, determining arterial blood pressure within the patient based on the aortic resistance value using a blood pressure determination system by
   retrieving at least one calibration value (K) relating aortic resistance to arterial blood pressure within the patient, and
   determining the arterial blood pressure based on the aortic resistance value (R) and the calibration value (K);
   wherein the calibration value (K) is representative of arterial pressure (P) multiplied by systemic resistance (R).

2. The method of claim 1
   wherein the implantable medical device includes a right atrial electrode and a device housing electrode positioned generally on opposing sides of the aorta of the patient; and
   wherein detecting aortic resistance (R) includes measuring electrical resistance between the right atrial electrode and the device housing electrode.

3. The method of claim 1 further including a calibration procedure for calculating K based on known values of patient pressure (P) and systemic resistance (R).

4. The method of claim 3 wherein the device is used in conjunction with an external arterial blood pressure detector and wherein the calibration procedure includes
   receiving a value representative of true patient blood pressure (P') from the external detector measured at a time t;
   detecting a value representative of patient aortic resistance (R'), the value also detected at about time t; and
   calculating K based on $K=P'R'$.

5. The method of claim 3 wherein the calibration procedure is performed periodically to update the value of K.

6. The method of claim 5 wherein the calibration procedure is performed monthly.

7. A method for use with an implantable medical device for detecting blood pressure, the method comprising:
   detecting a value representative of aortic electrical resistance (R) within the patient using a detector; and
   in the implantable medical device, determining arterial blood pressure within the patient based on the aortic resistance value using a blood pressure determination system by
   retrieving at least one calibration value (K) relating aortic resistance to arterial blood pressure within the patient, and
   determining the arterial blood pressure based on the aortic resistance value (R) and the calibration value (K); and
   wherein determining arterial blood pressure within the patient based on the aortic resistance value (R) and the calibration value (K) is performed by calculating:

$P=K/R$.

8. The method of claim 1 wherein determining arterial blood pressure within the patient based on the aortic resistance value (R) and the calibration value (K) is performed substantially continuously based on newly detected values of aortic resistance.

9. A method for use with an implantable medical device for detecting blood pressure, the method comprising:
   detecting a value representative of aortic electrical resistance (R) within the patient using a detector;
   in the implantable medical device, determining arterial blood pressure within the patient based on the aortic resistance value using a blood pressure determination system by
   retrieving at least one calibration value (K) relating aortic resistance to arterial blood pressure within the patient,
   determining the arterial blood pressure based on the aortic resistance value (R) and the calibration value (K); and
   further including:
   determining a value representative of the autonomic tone of the patient; and
   adjusting the calibration value to compensate for changes in autonomic tone before determining the arterial pressure.

10. The method of claim 9 wherein determining a value representative of the autonomic tone of the patient includes detecting a proxy for autonomic tone including one or more of: heart rate, heart rate variability, and direct measures of sympathetic electrical activity within the patient.

11. A method for use with an implantable medical device for detecting blood pressure, the method comprising:
    detecting a value representative of aortic electrical resistance (R) within the patient using a detector; and in the implantable medical device, determining arterial blood pressure within the patient based on the aortic resistance value using a blood pressure determination system by retrieving at least one calibration value (K) relating aortic resistance to arterial blood pressure within the patient, and determining the arterial blood pressure based on the aortic resistance value (R) and the calibration value (K) and further including identifying maximum and minimum values of aortic resistance based on a plurality of measurements taken over a time period corresponding to a patient heart beat;

receiving separate values representative of systolic and diastolic pressure from an external system obtained during the same heart beat; and calibrating the arterial blood pressure determination based on the maximum and minimum values of aortic resistance in combination with the values representative of systolic and diastolic pressure.

12. The method of claim 1 further including:
receiving a value representative of systemic resistance ($R_a$) from an external system; and
determining stroke volume based on a comparison of the systemic resistance value and an arterial blood pressure value determined by an implantable medical device.

13. The method of claim 1 further including the step of determining stroke volume based, in part, on arterial pressure.

14. The method of claim 13 further including:
detecting a value representative of patient heart rate using an implantable medical device; and
determining cardiac output based on a comparison of patient heart rate and stroke volume.

15. The method of claim 1 further including the step of detecting changes in the hematocrit of the patient based on the aortic resistance.

16. The method of claim 1 further including delivering therapy in response to changes in arterial pressure.

* * * * *

UNITED STATES PATENT AND TRADEMARK OFFICE
CERTIFICATE OF CORRECTION

PATENT NO.       : 7,654,964 B1                                    Page 1 of 1
APPLICATION NO.  : 11/378604
DATED            : February 2, 2010
INVENTOR(S)      : Kroll et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Twenty-third Day of November, 2010

David J. Kappos
*Director of the United States Patent and Trademark Office*